United States Patent [19]

Haining

[11] Patent Number: 4,790,822
[45] Date of Patent: Dec. 13, 1988

[54] RETRACTABLE HYPODERMIC SAFETY SYRINGE

[76] Inventor: Michael L. Haining, 6731 Ashmore, Houston, Tex. 77069

[21] Appl. No.: 131,631

[22] Filed: Dec. 11, 1987

[51] Int. Cl.⁴ .............................................. A61M 5/00
[52] U.S. Cl. ..................................... 604/110; 604/195
[58] Field of Search ............... 604/198, 196, 195, 194, 604/187, 218, 220, 110, 222, 218

[56] References Cited

U.S. PATENT DOCUMENTS

| | | | |
|---|---|---|---|
| 3,354,882 | 11/1967 | Coanda | 604/222 |
| 4,562,844 | 1/1986 | Carpenter et al. | 604/220 |
| 4,643,200 | 2/1987 | Jennings, Jr. | 604/198 X |
| 4,675,005 | 6/1987 | DeLuccia | 604/198 X |
| 4,692,156 | 9/1987 | Haller | 604/110 X |
| 4,747,830 | 5/1988 | Gloyer | 604/110 |

Primary Examiner—John D. Yasko
Attorney, Agent, or Firm—Richard L. Moseley

[57] ABSTRACT

A disposable hypodermic syringe is provided having a needle carrier that is retractable into the barrel by the plunger after use for anti-pricking protection. Additionally the needle carrier is locked to the plunger to prevent any further use of the syringe. After the needle carrier is locked into the rectractable position, the plunger may be broken off even with the barrel so that the needle may not be accidentally pushed out of the barrel and become exposed.

5 Claims, 3 Drawing Sheets

RETRACTABLE HYPODERMIC SAFETY SYRINGE

BACKGROUND OF THE INVENTION

Disposable hypodermic syringes have been available for a number of years, basically due to the decrease in the cost of the hypodermic needle itself. These disposable hypodermic needles are contemplated for only on use and generally come with a protective sleeee over the needle. The protective sleeve provides protection against accidental pricking, both before and after use. The protective sleeve has to be removed before use and replaced after use to provide the necessary protection.

With the advent of the AIDS virus, which may be transmitted by a contaminated needle, there has arise a need for a safer anti-pricking disposable hypodermic syringe. A need has also arisen for a secure means to prevent repeated use of a disposable syringe and possible contamination.

SUMMARY OF THE INVENTION

In view of the above considerations there is provided a disposable hypodermic syringe with a needle carried by a needle carrier that is retractable into the barrel after use for anti-pricking protection. Additionally, the hypodermic syringe plunger is locked to the needle carrier to prevent any further use of the syringe. After the needle carrier and needle are locked into the retractable position, the plunger may be be broken-off even with the barrel so that the needle may not be accidentally pushed out of the barrel and become expodsed again.

DESCRIPTION OF THE PREFERRED EMBODIMENT OF THE INVENTION

The invention will now be further described with reference to the accompanying drawings.

Figure 1:
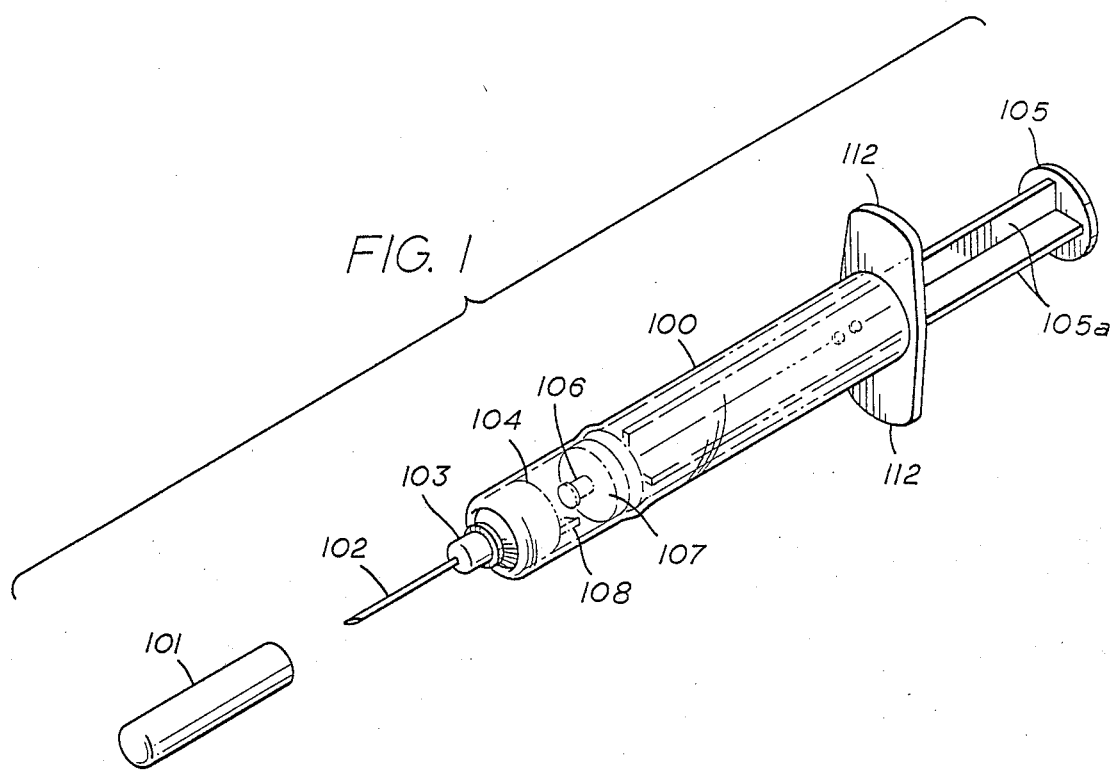
FIG. 1 is a perspective view of the disposable hypodermic syringe of the present invention.

In FIG. 1 is shown a perspective view of the hypodermic syringe of the present invention. The syringe is shown to have a barrel 100. Into one end of the barrel is placed a plunger 105 and into the other end is placed a needle carrier 104. A hypodermic needle 102 is connected to the carrier by a standard connection 103. A protective sleeve 101 is provided to prevent pricking or contamination before use.

The needle carrier is held in place in the barrel by shoulders 108 as shown. Also shown in the drawing in FIG. 1 are adjuncts to the plunger 106 and 107 which will be explained in more detail. Standard syringe finger flanges 112 are provided to hold the barrel.

Figure 2:
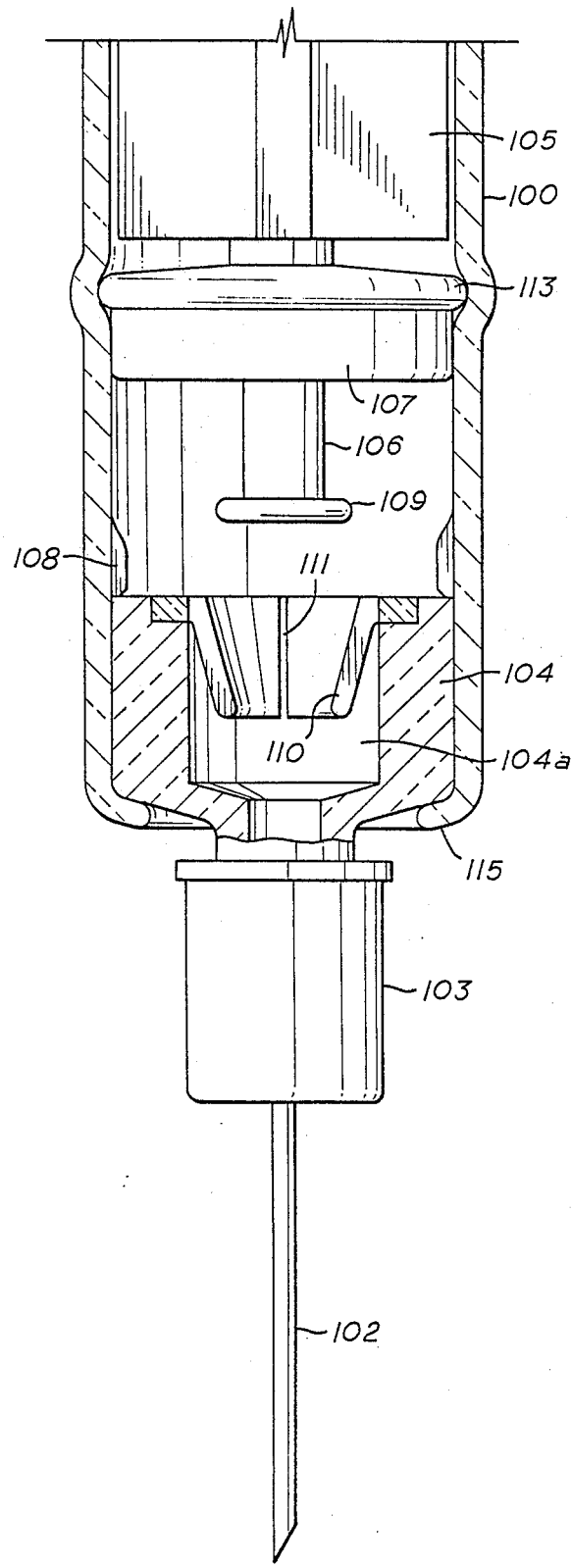
FIG. 2 is a plan view in cross section of the lower end of the disposable hypodermic syringe of the present invention.

Referring now to FIG. 2, the lower end of the hypodermic syringe of the present invention is shown. The lower end of the barrel is formed into tw inwardly extending lips 115, which support the needle carrier 104. The hypodermic needle 102 is connected to needle carrier 104 by ordinary means 103 such as screws, threads, or other conventional needle attachment methods. The needle carrier 104 includes cavity 104a and extending into the cavity is a frusto-conical snap locking ring 110. The locking ring is affixed to the needle carrier such that the cones are tapering inward and toward the needle attachment end of the carrier. The snap ring is separated into four pieces by slots 111 which allows the snap ring to be slightly resilient. The entrre needle and needle carrier is held in place within the barrel by opposing shoulders 108 which extend inwardly fromtthe inside wall of the barrel. It will be readily appreciated that the needle and needle carrier could be held inside the barrel simply by a friction fit precluding the need of the shoulders 108. However, these shoulders, do provide better support for the needle carrier within the barrel.

Now looking at the lower end of the plunger 105, there is noted a sealing member 113 which engages the inner wall of the barrel and slightly distorts the semi-rigid wall of the barrel. hhe actual distortion of the barrel is not nearly so much as that being shown for emphasis in the drawing.

Directly above the seal member is a piston 107, the purpose of which will become readily apparent. Extending from the plunger is a projection 106 with a T-type head 109 at the end of the projection.

Figure 3:
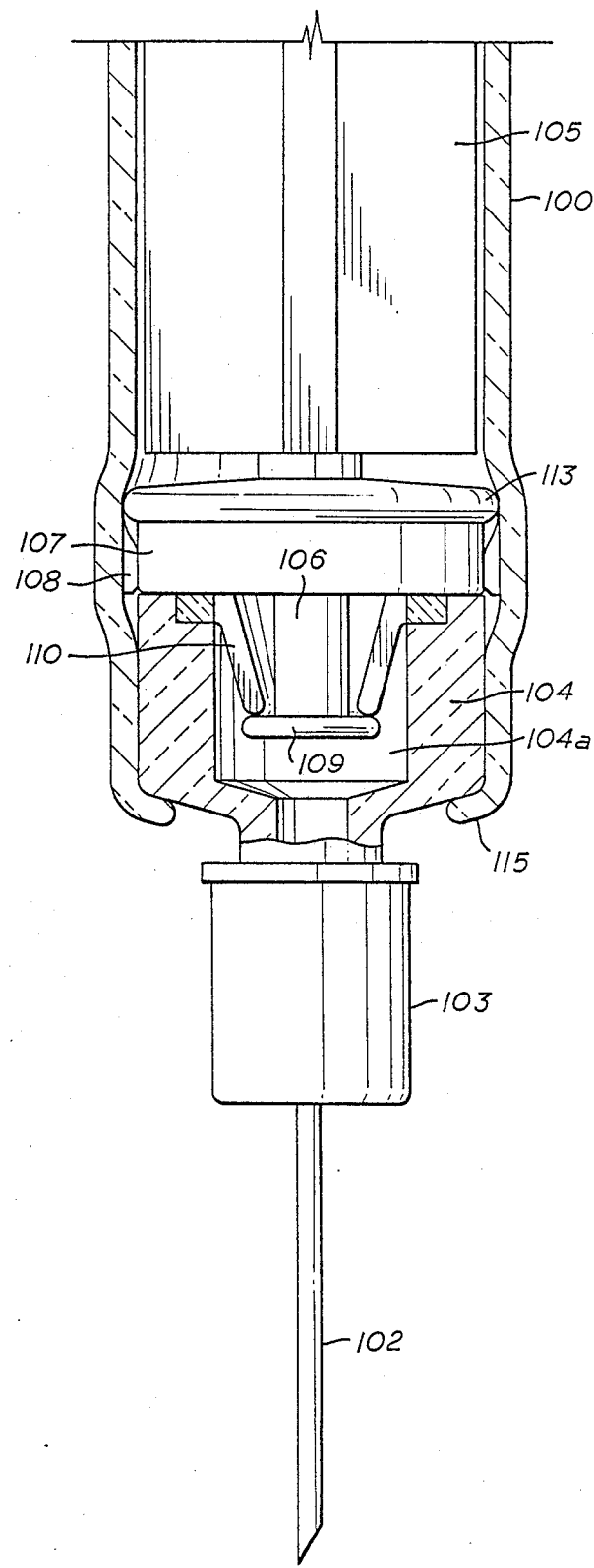
FIG. 3 is a plan view in cross section showing the plunger engaging the needle carrier.

Referring now to FIG. 3, the plunger 105 has been completely depressed into the barrel. Projection 106 with head 109 has pushed open the frusto-conical snap locking ring 110 and the head 109 is engaged by the ends of the locking ring. At the same time, the piston 107 has pushed against shoulders 108 in the wall of the barrel to distort the wall somewhat and move these shoulders aside.

Figure 4:
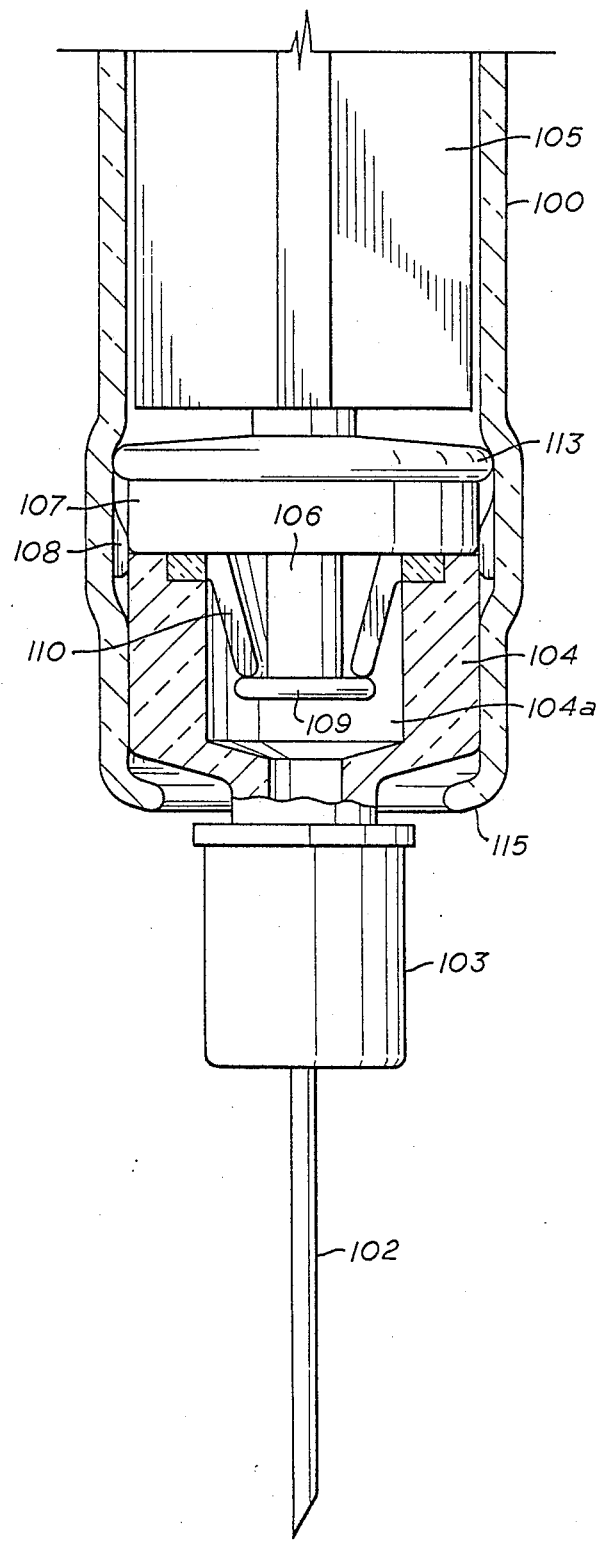
FIG. 4 is a plan view in cross section showing the plunger engaging the retaining shoulders and the retraction of the needle carrier.
Figure 5:
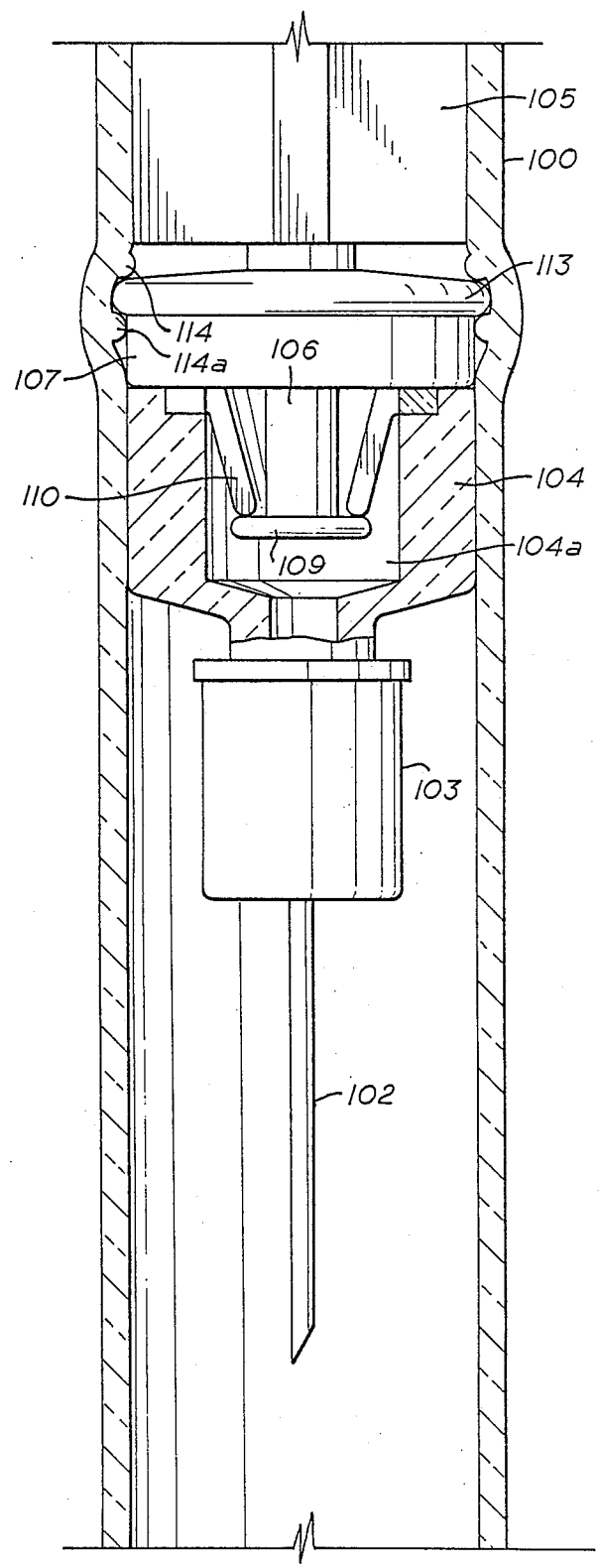
FIG. 5 is a plan view in cross section showing the needle and needle carrier locked in the retracted position.

In FIG. 4 the plunger has been moved upward in the barrel pulling the needle carrier up against the shoulders 108 as shown. The action of the piston 107 allows the carrier to slide past the shoulders 108. FIG. 5 shows the needle and needle carrier completely retracted into the barrel. Provided in the upper end of the barrel are two inner ridges 114 and 114a which lock the sealing ring 113 into place. As can be noted in FIG. 5 the barrel wall 100a above the locking ridges 114, 114a is somewhat thicker than the barrel wall 100b below the locking ridges. This thickness of wall prevents the barrel from any uurther distortion above these locking ridges and prevents the needle and plunge from being completely withdrawn from the barrel.

Figure 6:
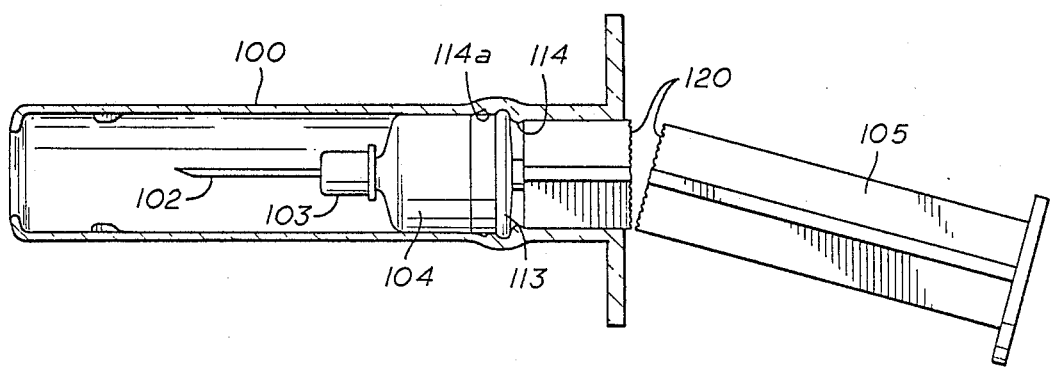
FIG. 6 is a plan view showing the needle and carrier in the retracted position with the plunger broken even with the barrel.

Referring now to FIG. 6, there is shown the needle 102 and needle carrier 104 completely retracted into the barrel 100. To prevent the plunger from being pressed back and re-exposing the needle there is provided a series of perforations around the plunger such that the plunger may be broken off even with finger flanges 112 when the seal 113 is seated between the locking ridges. There is thus provided a completely safe retractable hypodermic needle.

The foregoing description of the invention has been directed to a particular preferred embodiment of the present invention for purposes of explanation and illustration. It will be apparent to those skilled in the art that many modification and changes in the apparatus may be made without departing from the scope and spirit of the invention. It is, therefore, intended that the following claims cover all equivalent modifications and variations as fall within the scope of the invention as defined by the claims.

What is claimed is:

1. In a hypodermic syringe having a plunger and a retractable needle carried on a needle carrier which fits by friction in one end of a barrel and wherein the needle carrier includes engaging means engageable with the plunger to retract the needle carrier and needle into the barrel, the improvement comprising:
   (a) providing said barrel with seimi-rigid deformable walls;
   (b) providing inwardly projecting shoulders in said barrel directly above said needle carrier to retain said needle carrier in place; and
   (c) providing said plunger with expanding means to deform said walls and said shoulders outward and release said carrier when said engaging means engages said plunger to allow said needle and needle carrier to be retracted into said barrel.

2. The hyprodermic syringe of claim 1 wherein said plunger is provided with a projection having a T type head, and said engaging means comprises a frusto-conical snap locking ring adapted to receive said head and lock said carrier to said plunger.

3. A hypodermic syringe having a retractable needle, comprising in combination:
   (a) a hollow cylindrical barrel of a semi-rigid deformable material open at both ends and having an inwardly projecting lip at one end;
   (b) a needle carrier carrying a hypodermic needle, said needle carrier being seated in said barrel on said lip such that said needle projects out of said barrel;
   (c) inwardly extending internal shoulders in said barrel disposed directly adjacent said needle carrier to retain said needle carrier in place;
   (d) a plunger slideably mounted in said barrel above said needle carrier;
   (e) engaging means on said needle carrier engageable with said plunger to lock said needle carrier to said plunger; and
   (f) expanding means on said plunger to deform said barrel with said shoulders outward and release said needle carrier when said engaging means engages said plunger.

4. The hypodermic syringe of claim 3 wherein said plunger is provided with a T type head, and said engaging means comprises a frusto-coical snap locking ring adapted to receive said head and lock said needle carrier to said plunger.

5. A hypodermic syringe having a retractable needle, comprising in combination:
   (a) a hollow cylindrical barrel of a semi-rigid deformable material open at both ends;
   (b) a needle carrier carrying a hypodermic needle, said needle carrier being fitted into one end of said barrel and held therein by friction and disposed such that said hypodermic needle projects out of said barrel;
   (c) a plunger slidably disposed within said barrel from the opposite end;
   (d) a projection on the end of said plunger adjacent said needle carrier, said projection having a T type head;
   (e) a frusto-conical snap locking ring on said needle carrier adjacent said plunger, said ring adapted to receive said head and lock said needle carrier to said plunger;
   (f) expanding means on said plunger to deform the inner walls of said barrel outward as said plunger slides in said barrel; and
   (g) inwardly projecting internal shoulders within said barrel abutting said needle carrier to hold said needle carrier in place within said barrel, said shoulders being deformable outward to release said needle carrier in response to said expanding means when said head locks into said ring.

* * * * *